United States Patent [19]

Bolton et al.

[11] Patent Number: 4,814,178

[45] Date of Patent: Mar. 21, 1989

[54] FLOATING SUSTAINED RELEASE THERAPEUTIC COMPOSITIONS

[76] Inventors: Sanford Bolton, 67 Phelps Ave., Cresskill, N.J. 07626; Philip H. Izevbehai, 169-15 89th Ave. - Apt. #2A, Jamaica, N.Y. 11432; Subhash Desai, 18-15 Deer Creek Dr., Plainboro, N.Y. 08536

[21] Appl. No.: 69,006

[22] Filed: Jul. 1, 1987

[51] Int. Cl.$^4$ .................. A61K 9/44; A61K 9/20; A61K 9/22

[52] U.S. Cl. .................. 424/467; 424/464; 424/468; 424/40; 424/484; 424/485

[58] Field of Search ............... 424/464, 467, 468, 469, 424/484, 485

[56] References Cited

U.S. PATENT DOCUMENTS

| | | | |
|---|---|---|---|
| 2,704,269 | 3/1955 | Tice | 426/576 |
| 3,065,143 | 11/1962 | Christenson et al. | 167/82 |
| 3,445,242 | 5/1969 | McDonnell | 426/576 |
| 3,574,820 | 4/1971 | Johnson et al. | 424/20 |
| 3,900,577 | 8/1975 | Haas | 426/576 |
| 3,939,001 | 2/1976 | Clausi et al. | 106/136 |
| 3,976,764 | 8/1976 | Watanabe | 424/19 |
| 4,055,178 | 10/1977 | Harrigan | 128/260 |
| 4,064,282 | 12/1977 | Hallstrom et al. | 426/576 |
| 4,126,672 | 11/1978 | Sheth et al. | 424/22 |
| 4,140,755 | 2/1979 | Sheth et al. | 424/21 |
| 4,167,558 | 9/1979 | Sheth et al. | 424/22 |
| 4,434,153 | 2/1984 | Urquahart et al. | 424/22 |
| 4,451,260 | 5/1984 | Mitra | 424/890 |

OTHER PUBLICATIONS

M. Nakano, Y. Nakamura, K. Takikawa, M. Kouketsu and T. Arita, J. Pharm. Pharmacol., 31, pp. 869–872 (1979).
M. Nakano, K. Takikawa, K. Juni and T. Arita, Chem. Pharm. Bull., 27, pp. 2834–2837 (1979).
M. Nakano, M. Kouketsu, Y. Nakamura and K. Juni, Chem. Pharm. Bull., 28, pp. 2905–2908 (1980), N. A. Boraie and V. F. Naggar, Acta Pharm. Jugosl., 34, pp. 247–256 (1984).
Nakano et al., J. Pharm. Pharmacol, 31: pp. 869–872 (1979).
Nakano et al., Chem. Pharam. Bull. 27(11): pp. 2834–2837 (1979).
Nakano et al., Chem. Pharm. Bull. 18(10) pp. 2905–2908(1980).
Boraie et al., Aeta Pharm. Jugosl. 34: pp. 247–256 (1984).

*Primary Examiner*—Shep K. Rose
*Attorney, Agent, or Firm*—Wyatt, Gerber, Burke and Badie

[57] ABSTRACT

Non-compressed sustained release tablets which will float on gastric fulid are described. The tablets comprise a hydrocolloid gelling agent, the selected therapeutic agent and water.

7 Claims, No Drawings

FLOATING SUSTAINED RELEASE THERAPEUTIC COMPOSITIONS

BACKGROUND OF THE INVENTION

1. Field of Invention

This invention relates to therapeutic compositions in unit dosage form which are capable of floating on gastric fluid and delivering their contained therapeutic agent over an extended period of time.

2. Description of the Prior Art

The convenience of administering a single dose of a medication which releases active ingredients over an extended period of time as opposed to the administration of a number of single doses at regular intervals has long been recognized in the pharmaceutical arts. The advantage to the patient and clinician in having consistent and uniform blood levels of medication over an extended period of time are likewise recognized.

The conventional approaches to sustained release can be disadvantageous when the medicament is administered orally because certain classes of active ingredients are not suited to absorption during passage through the gastrointestinal tract due to their physiochemical properties and/or favorable sites of absorption. Penicillin, for example, is fully absorbed at one point in the intestine. Once the dosage unit containing pencillin passes this point under the influence of peristaltic movement, the remaining penicillin is not absorbed into the blood stream, but is excreted.

Most medicaments will undergo varying degrees of change in solubility by passage from the strongly acid conditions of the stomach to the neutral and to the alkaline conditions of the intestines. Additionally, there are medicaments, e.g. antacids which are intended to act in the stomach and therefore lose most beneficial properties when they pass into the intestine.

The advantages of sustained release dosage forms, which are retained in the stomach, for example, by floating in the gastric fluid, slowly releasing their therapeutic contents into the gastric fluid for passage through the intestinal tract, will be readily apparent. These include (1) increased contact time for local activity in the stomach, where such is required, as in the treatment of stomach ulcers, (2) increased and more efficient absorption for drugs which have specific absorption sites, and (3) the ability to reduce the number of dosages.

A number of patents disclose therapeutic dosage forms which float on the gastric fluid and have sustained release capabilities. In a series of U.S. Patents: (U.S. Pat. Nos. 4,126,672; 4,140,755; 4,167,558), Sheth and Tossounian claim compressed tablets and capsules containing from about 20% to about 75% by weight of one or a mixture of hydrocolloids as carriers for therapeutic agents. The hydrocolloids recited in the examples and in the claims are cellulose derivatives including methylcellulose, hydroxyalkylcelluloses and carboxymethyl-cellulose. The products are said to be in hydrodynamic balance so that, upon contact with gastric fluid, the hydrocolloids hydrate and acquire a bulk density of less than one, thereby being buoyant in the gastric fluid. The presence of pharmaceutically inert fatty materials having a specific gravity of less than one decreases the hydrophilicity and increases the buoyancy of the dosage form.

Urquhart and Theeuwes in U.S. Pat. No. 4,434,153 describes a prolonged release system in which coated tiny pills comprising a wall of "drug release rate controlling" wax surrounding a core of medicament, are dispersed in a hydrophilic matrix and compressed to a tablet in which the matrix swells in stomach fluid for extended residency therein.

Mitra in U.S. Pat. No. 4,451,260 described a sustained release device which is a multilayer composite comprising a carrier film which is water-insoluble and contains a medicament and a barrier film comprising a water-insoluble, water- and medicament-permeable polymer. The two films are sealed in such a way as to entrap a plurality of small pockets of air between said films. The air-containing composite has a bulk density of less than one so as to render it buoyant in gastric fluid. The composite film is cut into desired lengths which are folded to fit inside a gelatin capsule. Upon oral administration, the capsule dissolves and the insoluble composite film floats on the gastric fluid.

Hydrophilic polymers or hydrocolloids have been used in sustained release dosage forms which have been prepared without compression.

The procedure disclosed by Nakano et al in J. Pharm. Pharmacol., 31, 869 (1979) and referred to in Chem. Pharm. Bull., 28, 2905 (1980), involves dissolving agar in water at 90° C. and, after the solution is cooled to 70° C., sulphamethizole is suspended in the agar solution. The drug suspension, containing about 6% agar and 8% drug is then extruded through a plastic syringe onto the top of a cold water-immiscible organic solvent such as ethyl acetate, to form drug-containing beads which are separated from the solvent by filtration and dried. The dried beads contain about 40% agar. There is no indication of the density of the beads or whether they can float on gastric fluid.

A procedure disclosed by Nakano et al in Chem. Pharm. Bull., 27, 2834 (1979) involves swelling konjac flour with water and extruding the resulting sol, containing 5% konjac, from a plastic syringe into boiling water saturated with calcium hydroxide. After a period of boiling, an elastic gel is obtained and is washed with water to remove the alkali. The gel is then placed at 70° C. into an ammoniacal solution containing 5% theophylline to permit the drug to permeate into the gel. The gel containing theophylline is then dried to constant weight and cut into pieces. The dried gel contains 55% konjac. There is no indication of the density of the dried gel or whether the pieces can float on gastric fluid.

Boraie and Naggar in Acta Pharm. Jugosl., 34, 247 (1984) disclose a procedure for preparing non-compressed tablets which involves preparing an aqueous suspension containing at least 7.5% agar and a medicament such as theophylline, at an agar/drug ratio of 1/0.5 to 1/1.33, and charging said suspension into a tablet mold and cooling. The molded tablets are removed from the mold and dried. The dried tablets have an agar content of at least 43%. There is no indication of the density of the dried tablets or whether they will float on gastric fluid.

It is noteworthy that, although Sheth and Tossounian (op cit) disclose the preparation of compressed tablets and capsules which float on gastric fluid, they specifically caution against the use of water or other solvent for the hydrocolloid. "In the practice of the invention, the hydrocolloid is incorporated into the formulation in dry form ... Wherein a hydrocolloid such as described herein is combined in the formulation in the presence of a solvent, such hydrocolloid does not function to facilitate the buoyancy of the tablets prepared therefrom" (U.S. Pat. No. 4,167,558, col. 5, lines 37-53).

Our co-pending U.S. application Ser. No. 722,832 filed Apr. 12, 1985, discloses non-compressed therapeutic compositions containing 0.5 to 4% gelling agent, 10 to 20% therapeutically acceptable inert oil and 50 to 75% therapeutic agent and capable of floating on gastric fluid and delivering their contained therapeutic agent over an extended period of time.

The present invention is directed toward an oil-free, non-compressed therapeutic composition in unit dosage form, having a low concentration of gelling agent and at least 75% therapeutic agent and capable of floating on gastric fluid, and providing sustained release of the therapeutic agent upon administration.

SUMMARY OF THE INVENTION

An object of the present invention is to provide a solid unit dosage form capable of floating on gastric juice and delivering a therapeutic agent incorporated therein over an extended period of time.

Another object of the present invention is to provide a therapeutic solid unit dosage form as a non-compressed tablet which has a bulk density of less than one and sufficient mechanical stability for production and handling.

A further object of the present invention is to provide a floating non-compressed tablet which contains at least 75% of a therapeutic agent.

It has now been found that these improvements in a therapeutic solid unit dosage form can be achieved by incorporating into the non-compressed tablet, in addition to at least 75% therapeutic agent, 2.0 to 6.5% gelling agent and water.

DETAILED DESCRIPTION OF THE INVENTION

According to the present invention, therapeutic dosage forms have now been discovered which are easy to prepare, provide sustained release of contained therapeutic agents and float on gastric fluid. These unit dosage forms, which are in the form of tablets, although not compressed, have sufficient mechanical stability and hardness so that they will withstand the normal stress of production, packaging and dispensing. They have a density which is less than one and sufficiently low so that they will float on gastric fluid. Typically, the density is from about 0.5 to 0.95.

The tablets contain as essential ingredients about 75 to about 92.5% therapeutic agent, about 2 to 6.5% of a gelling agent and water. All percentages by weight in this disclosure and claims are based on total weight.

Except for those which must be protected from the gastric fluid, there is practically no limitation to the therapeutic agents which can be administered in accordance with this invention. They include, for example, analgesics, anorexias, antacids, antibiotics, antidiabetics, antihistamines, steroids, antinauseants, antispasmodies, cardiovascular preparations, decongestants, diuretics, geriatrics, muscle relaxants, tranquilizers and vitamins. More specific examples include theophylline, acetaminophen, ampicillin, atropine, penicillin, tetracycline, chlorathiazide, phenytoin, riboflavin, quinidine, cimetidine, captopril, indomethicin, prednisolone and estradiol. The agents can be employed as free bases or as metal or acid addition salts.

The gelling agents which may be used in the present invention are hydrocolloids, i.e. materials capable of absorbing aqueous fluids and undergoing swelling. The effective hydrocolloids are well known in the art and include agar and agarose and mixtures of locust bean gum with these and other hydrocolloids including carrageenan, alginic acid and its salts, konjac gum and the like. Surprisingly, locust bean gum, carrageenan and alginic acid do not product floating compositions when used as the sole gelling agent. The concentration of gelling agent in the non-compressed tablet is about 2 to 6.5% by weight of the total weight of the tablet.

The low concentration of gelling agents which are effective in the tablets of this invention are unexpected in view of the significantly higher concentrations disclosed in the prior art in both compressed and non-compressed tablets as well as capsules, gels and beads.

The tablet may also contain other conventional additives and excipients such as thickening agents, surfactants, preservatives, bulking agents and antioxidants.

The tablets of this invention have a density of less than one and will float on gastric fluid in vivo. They are sustained release dosage units, i.e. they release their medicaments over an extended period of time. The actual rate of release varies principally with the selected therapeutic agent and with the amount of exposed surface area and, therefore, with size and shape of the tablet.

The non-compressed tablets of the present invention may be prepared by the following method:

1. Prepare a solution of one or a mixture of hydrocolloid gelling agents and excipients, if any, in hot water;
2. Cool the solutin of gelling agent, but not to the point where gelation takes place;
3. Add the therapeutic agent to the gelling agent solution from step (2) while maintaining the temperature above the gelation temperature and stirring;
4. Pour the mixture from step (3) into a tablet mold and allow to stand in the mold to form a gel; and
5. Dry the molded gel tablets to reduce the water content.

The solution temperature for the gelling agent is generally about 70° to 100° C. and the pour temperature of the mixture is about 50° to 70° C. The specific temperature depends upon the gelling agent used in the formulation.

Variations of this procedure will be readily apparent to those skilled in the art.

The concentration of the various components in the aqueous mixture is 0.5 to 4% gelling agent, 25 to 40% therapeutic agent, optional amounts of excipients and the balance is water. The mixture is free of the inert oil disclosed in prior art compositions and consequently the dried tablet prepared therefrom is free of the inert oil.

During the gelation and drying steps, most of the water evaporates. The resulting product, although it is not compressed, is a hard tablet in the shape of the mold. Its hardness and compression strength, as well as friability, are comparable to those of most commercially available compressed therapeutic tablets. It is characterized by a network of multitudinous air holes and passages. It is surprising to find that such small quantitites of gelling agents are capable of forming such rugged tablets without compression.

The following examples are given by way of illustration only and are not to be considered limitations of this invention, many apparent variations of which are possible without departing from the spirit or scope thereof.

EXAMPLE 1

Theophylline tablets were prepared from the following formulation, using agar as gelling agent:

| Ingredients | grams | % |
| --- | --- | --- |
| Theophylline | 12.0 | 37.0 |
| Agar | 0.4 | 1.2 |
| Water | 20.0 | 61.7 |

Water and agar were charged into a beaker, stirred and heated to effect solution. The agar solution was cooled to 50° C. and the theophylline was gradually added and mixed with a mechanical stirrer for 5 to 10 minutes to form a milky suspension. The latter was poured at 50° C. into a tablet mold. The mold was covered and allowed to cool. Gelation occurred in 10 to 15 minutes. The tablets were removed from the mold and air dried on a screen for 24 hours.

The average tablet size was 11.1×4.8 mm and the average tablet weight was 233 mg. The average tablet density was 0.543 and the hardness, as determined with a Pfizer hardness tester, was 6.7 kg.

The composition of the dried tablets, as determined by extraction and analysis, was as follows:

| Ingredients | mg | % |
| --- | --- | --- |
| Theophylline | 205.0 | 88.0 |
| Agar | 6.6 | 2.8 |
| Water | 21.4 | 9.2 |

The release of theophylline from the tablets was determined using the U.S. Pharmacopeia basket method at 50 rpm and 37° C. The dissolution medium was at pH 1.3 (concentrated HCl diluted with distilled water to 0.1N).

| Time, hours | % Released | Cumulative % |
| --- | --- | --- |
| 1 | 25 | 25 |
| 2 | 8 | 33 |
| 3 | 7 | 40 |
| 4 | 5 | 45 |
| 5 | 6 | 51 |
| 6 | 4 | 55 |
| 8 | 6 | 61 |
| 10 | 5 | 66 |
| 12 | 5 | 71 |
| 24 | 23 | 94 |

EXAMPLE 2

Theophylline tablets were prepared as described in Example 1, using agar as gelling agent, in the following formulation:

| Ingredients | grams | % |
| --- | --- | --- |
| Theophylline | 12.0 | 36.8 |
| Agar | 0.6 | 1.8 |
| Water | 20.0 | 61.3 |

The molded gel tablets were air dried for 24 hours. The size of the dry tablet was 11.1×4.8 mm and the average weight was 237 mg per tablet. The tablet hardness was 6.2 kg and the average tablet density was 0.516.

The dried tablets had the following composition:

| Ingredients | mg | % |
| --- | --- | --- |
| Theophylline | 207.5 | 87.5 |
| Agar | 10.4 | 4.4 |
| Water | 19.2 | 8.1 |

The dissolution test was carried out by the basket method at 50 rpm and 37° C. in a 0.1N HCl dissolution medium (pH 1.3). The floating tablets had the following release pattern:

| Time, hours | % Released | Cumulative % |
| --- | --- | --- |
| 1 | 22 | 22 |
| 2 | 8 | 30 |
| 3 | 7 | 37 |
| 5 | 14 | 51 |
| 6 | 3 | 54 |
| 8 | 4 | 58 |
| 10 | 5 | 63 |
| 12 | 5 | 68 |
| 24 | 24 | 92 |

EXAMPLE 3

Theophylline tablets were prepared as described in Example 1, using agar as the gelling agent, in the following formulation:

| Ingredients | grams | % |
| --- | --- | --- |
| Theophylline | 12.0 | 36.6 |
| Agar | 0.8 | 2.4 |
| Water | 20.0 | 61.0 |

The molded gel tablets were air dried for 24 hours. The size of the dry tablet was 11.1×4.8 mm and the average tablet weight was 239 mg. The tablet hardness was 6.7 kg and the average tablet density was 0.548.

The dried tablets had the following composition:

| Ingredients | mg | % |
| --- | --- | --- |
| Theophylline | 210.0 | 87.9 |
| Agar | 13.8 | 5.8 |
| Water | 15.0 | 6.3 |

The dissolution test was carried out as described in Example 1. The floating tablets had the following release pattern:

| Time, hours | % Released | Cumulative % |
| --- | --- | --- |
| 1 | 20 | 20 |
| 2 | 9 | 29 |
| 3 | 7 | 36 |
| 5 | 14 | 50 |
| 6 | 3 | 53 |
| 8 | 5 | 58 |
| 10 | 5 | 63 |
| 12 | 5 | 68 |
| 24 | 24 | 92 |

EXAMPLE 4

Theophylline tablets were prepared as described in Example 1, using agar as the gelling agent and lactose as bulking agent, in the following formulation, in which the lactose was mixed with the theophylline before addition to the hot agar solution:

| Ingredients | grams | % |
| --- | --- | --- |
| Theophylline | 12.0 | 32.8 |
| Agar | 0.6 | 1.6 |
| Lactose | 4.0 | 10.9 |
| Water | 20.0 | 54.6 |

The molded gel tablets were air dried for 24 hours. The size of the dry tablet was 11.1×4.8 mm and the average tablet weight was 232 mg. The tablet hardness was 8.2 kg and the average tablet density was 0.602.

The dissolution test was carried out by the basket method at 50 rpm and 37° C. in a 0.1N HCl dissolution medium (pH 1.3). The floating tablets had the following release pattern:

| Time, hours | % Released | Cumulative % |
| --- | --- | --- |
| 1 | 27 | 27 |
| 2 | 10 | 37 |
| 3 | 7 | 44 |
| 4 | 6 | 50 |
| 6 | 8 | 58 |
| 8 | 9 | 67 |
| 10 | 7 | 74 |
| 12 | 6 | 80 |
| 24 | 17 | 97 |

EXAMPLE 5

Theophylline tablets were prepared as described in Example 1, using agar as the gelling agent and calcium gluconate as the hardening agent, in the following formulation, in which the calcium gluconate was mixed with the agar before preparation of the solution to which the theophylline was added:

| Ingredients | grams | % |
| --- | --- | --- |
| Theophylline | 12.0 | 36.1 |
| Agar | 0.6 | 1.8 |
| Calcium gluconate | 0.6 | 1.8 |
| Water | 20.0 | 60.2 |

The molded gel tablets were air dried for 24 hours. The tablet size was 11.1×4.8 mm and the average tablet weight was 226 mg. The tablet hardness was 8.0 kg and the average tablet density was 0.554.

The dissolution test, carried out at 50 rpm and 37° C. at pH 1.3, showed the following release pattern:

| Time, hours | % Released | Cumulative % |
| --- | --- | --- |
| 1 | 21 | 21 |
| 2 | 9 | 30 |
| 3 | 8 | 38 |
| 4 | 6 | 44 |
| 6 | 7 | 51 |
| 8 | 8 | 59 |
| 10 | 5 | 64 |
| 12 | 5 | 69 |
| 24 | 23 | 92 |

EXAMPLE 6

Theophylline tablets were prepared as described in Example 1, using a 2:1 mixture of agar and locust bean bum as the gelling agent, in the following formulation, in which the agar and locust bean gum were mixed before preparation of the solution to which the theophylline was added:

| Ingredients | grams | % |
| --- | --- | --- |
| Theophylline | 12.0 | 36.8 |
| Agar | 0.4 | 1.2 |
| Locust bean gum | 0.2 | 0.6 |
| Water | 20.0 | 61.3 |

The molded gel tablets were air dried for 24 hours. The dry tablet size was 10.46×4.41 mm and the average tablet weight was 235 mg. The tablet hardness was 8.1 kg and the average tablet density was 0.62.

Analysis of several dried tablets indicated the following composition:

| Ingredients | mg | % |
| --- | --- | --- |
| Theophylline | 215.5 | 91.9 |
| Agar | 7.0 | 3.0 |
| Locust bean gum | 3.5 | 1.5 |
| Water | 8.6 | 3.7 |

The dissolution test, carried out by the basket method at 50 rpm and 37° C. in a 0.1N HCl dissolution medium, showed that the floating tablets had the following release pattern:

| Time, hours | % Released | Cumulative % |
| --- | --- | --- |
| 1 | 18 | 18 |
| 2 | 8 | 26 |
| 3 | 6 | 32 |
| 4 | 5 | 37 |
| 6 | 8 | 45 |
| 8 | 7 | 52 |
| 10 | 11 | 63 |
| 12 | 4 | 67 |
| 24 | 27 | 94 |

EXAMPLE 7

Theophylline tablets were prepared as described in Example 1, using a 1:2 mixture of alginic acid and locust bean gum as the gelling agent, in the following formulation:

| Ingredients | grams | % |
| --- | --- | --- |
| Theophylline | 12.0 | 36.8 |
| Alginic acid | 0.2 | 0.6 |
| Locust bean gum | 0.4 | 1.2 |
| Water | 20.0 | 61.3 |

The molded gel tablets were air dried for 24 hours. The size of the dry tablet was 11.1×4.8 mm and the average tablet weight was 236 mg. The tablet hardness was 8.8 kg and the average tablet density was 0.574.

The dried tablets had the following composition:

| Ingredients | mg | % |
| --- | --- | --- |
| Theophylline | 209.5 | 88.9 |
| Alginic acid | 3.4 | 1.4 |
| Locust bean gum | 6.8 | 2.9 |
| Water | 15.9 | 6.7 |

The dissolution test at 37° C. at pH 1.3 showed the floating tablets had the following release pattern:

| Time, hours | % Released | Cumulative % |
|---|---|---|
| 1 | 20 | 20 |
| 2 | 8 | 28 |
| 3 | 6 | 34 |
| 4 | 5 | 39 |
| 5 | 3 | 42 |
| 6 | 4 | 46 |
| 8 | 7 | 53 |
| 10 | 6 | 59 |
| 12 | 6 | 65 |
| 24 | 19 | 84 |

EXAMPLE 8

Theophylline tablets were prepared as described in Example 1, using a 2:1 mixture of alginic acid and locust bean gum as the gelling agent, in the following formulation:

| Ingredients | grams | % |
|---|---|---|
| Theophylline | 12.0 | 36.8 |
| Alginic acid | 0.4 | 1.2 |
| Locust bean gum | 0.2 | 0.6 |
| Water | 20.0 | 61.3 |

The molded gel tablets were air dried for 24 hours. The dry tablet size was 10.76×4.46 mm and the average tablet weight was 250 mg. The tablet hardness was 8.9 kg and the average tablet density was 0.599.
The dried tablets had the following compositon:

| Ingredients | mg | % |
|---|---|---|
| Theophylline | 228.0 | 91.3 |
| Alginic acid | 7.4 | 3.0 |
| Locust bean gum | 3.7 | 1.5 |
| Water | 10.7 | 4.3 |

The floating tablets had the following release pattern at 37° C. at pH 1.3:

| Time, hours | % Released | Cumulative % |
|---|---|---|
| 1 | 25 | 25 |
| 2 | 9 | 34 |
| 3 | 7 | 41 |
| 4 | 6 | 47 |
| 5 | 5 | 52 |
| 6 | 4 | 56 |
| 8 | 7 | 63 |
| 10 | 6 | 69 |
| 12 | 4 | 73 |
| 24 | 20 | 93 |

EXAMPLE 9

Theophylline tablets were prepared as described in Example 1, using a 1:1 mixture of alginic acid and locust bean gum as the gelling agent in the following formulation:

| Ingredients | grams | % |
|---|---|---|
| Theophylline | 12.0 | 36.6 |
| Alginic acid | 0.4 | 1.2 |
| Locust bean gum | 0.4 | 1.2 |
| Water | 20.0 | 61.0 |

The molded gel tablets were air dried for 24 hours. The size of the dry tablet was 11.1×4.8 mm and the average tablet weight was 238 mg. The tablet hardness was 8.7 kg and the tablet density was 0.572.
The tablets had the following composition:

| Ingredients | mg | % |
|---|---|---|
| Theophylline | 212.5 | 89.1 |
| Alginic acid | 7.0 | 2.9 |
| Locust bean gum | 7.0 | 2.9 |
| Water | 11.9 | 5.0 |

The floating tablets had the following release pattern at 50 rpm at 37° C. at pH 1.3:

| Time, hours | % Released | Cumulative % |
|---|---|---|
| 1 | 24 | 24 |
| 2 | 11 | 35 |
| 3 | 7 | 42 |
| 4 | 6 | 48 |
| 6 | 10 | 58 |
| 8 | 6 | 64 |
| 10 | 6 | 70 |
| 12 | 4 | 74 |
| 24 | 22 | 96 |

EXAMPLE 10

Theophylline tablets were prepared as described in Example 1, using a 1:1 mixture of iota carrageenan and locust bean gum as the gelling agent, in the following formulation:

| Ingredients | grams | % |
|---|---|---|
| Theophylline | 12.0 | 37.0 |
| Iota carrageenan | 0.2 | 0.6 |
| Locust bean gum | 0.2 | 0.6 |
| Water | 20.0 | 61.7 |

The molded gel tablets were air dried for 24 hours. The dry tablet size was 11.1×4.8 mm and the average tablet weight was 220 mg. The tablet hardness was 6.5 kg and the average tablet density was 0.521.
The dissolution test at 50 rpm and 37° C. at pH 1.3 showed the floating tablets had the following release pattern:

| Time, hours | % Released | Cumulative % |
|---|---|---|
| 1 | 15 | 15 |
| 2 | 8 | 23 |
| 3 | 7 | 30 |
| 4 | 5 | 35 |
| 6 | 9 | 44 |
| 8 | 8 | 52 |
| 10 | 6 | 58 |
| 12 | 5 | 63 |
| 24 | 31 | 94 |

EXAMPLE 11

Theophylline tablets were prepared as described in Example 1, using a 1:2 mixture of iota carrageenan and locust bean bum as the gelling agent, in the following formulation:

| Ingredients | grams | % |
|---|---|---|
| Theophylline | 12.0 | 36.8 |
| Iota carrageenan | 0.2 | 0.6 |

-continued

| Ingredients | grams | % |
|---|---|---|
| Locust bean gum | 0.4 | 1.2 |
| Water | 20.0 | 61.3 |

The molded gel tablets were air dried for 24 hours. The dry tablet size was 11.1×4.8 mm and the average tablet weight was 234 mg. The tablet hardness was 8.3 kg and the average tablet density was 0.515.

The floating tablets had the following release pattern in the dissolution test carried out by the basket method at 50 rpm and 37° C. in a 0.1N HCl dissolution medium at pH 1.3:

| Time, hours | % Released | Cumulative % |
|---|---|---|
| 1 | 18 | 18 |
| 2 | 8 | 26 |
| 3 | 7 | 33 |
| 4 | 6 | 39 |
| 6 | 9 | 48 |
| 8 | 8 | 56 |
| 10 | 5 | 61 |
| 12 | 6 | 67 |
| 24 | 29 | 96 |

EXAMPLE 12

Theophylline tablets were prepared as described in Example 1, using a 2:1 mixture of iota carrageenan and locust bean gum as the gelling agent, in the following formulation:

| Ingredients | grams | % |
|---|---|---|
| Theophylline | 12.0 | 36.8 |
| Iota carrageenan | 0.4 | 1.2 |
| Locust bean gum | 0.2 | 0.6 |
| Water | 20.0 | 61.3 |

The molded gel tablets were air dried for 24 hours. The dry tablet size was 10.77×4.55 mm and the average tablet weight was 237 mg. The tablet hardness was 8.0 kg and the average tablet density was 0.572.

The dissolution test at 37° C. at pH 1.3 showed the floating tablets had the following release pattern:

| Time, hours | % Released | Cumulative % |
|---|---|---|
| 1 | 17 | 17 |
| 2 | 7 | 24 |
| 3 | 5 | 29 |
| 4 | 5 | 34 |
| 6 | 9 | 43 |
| 8 | 9 | 52 |
| 10 | 5 | 57 |
| 12 | 7 | 64 |
| 24 | 35 | 99 |

EXAMPLE 13

Theophylline tablets were prepared as described in Example 1, using a 1:1 mixture of iota carrageenan and locust bean gum as the gelling agent, in the following formulation:

| Ingredients | grams | % |
|---|---|---|
| Theophylline | 12.0 | 36.6 |
| Iota carrageenan | 0.4 | 1.2 |

-continued

| Ingredients | grams | % |
|---|---|---|
| Locust bean gum | 0.4 | 1.2 |
| Water | 20.0 | 61.0 |

The molded gel tablets were air dried for 24 hours. The dry tablet size was 11.1×4.8 mm and the average tablet weight was 227 mg. The tablet hardness was 10.0 kg and the average tablet density was 0.567.

EXAMPLE 14

Theophylline tablets were prepared as described in Example 1, using a 1:1 mixture of kappa carrageenan and locust bean gum as the gelling agent, in the following formulation:

| Ingredients | grams | % |
|---|---|---|
| Theophylline | 12.0 | 37.0 |
| Kappa carrageenan | 0.2 | 0.6 |
| Locust bean gum | 0.2 | 0.6 |
| Water | 20.0 | 61.7 |

The molded gel tablets were air dried for 24 hours. The dry tablet size was 11.1×4.8 mm and the average tablet weight was 219 mg. The tablet hardness was 6.1 kg and the average tablet density was 0.515.

The dissolution test at 50 rpm and 37° C. at pH 1.3 showed the floating tablets had the following release pattern:

| Time, hours | % Released | Cumulative % |
|---|---|---|
| 1 | 29 | 29 |
| 2 | 19 | 48 |
| 3 | 16 | 64 |
| 4 | 16 | 80 |
| 6 | 16 | 96 |
| 8 | 4 | 100 |

EXAMPLE 15

Theophylline tablets were prepared as described in Example 1, using a 1:2 mixture of kappa carrageenan and locust bean gum as the gelling agent, in the following formulation:

| Ingredients | grams | % |
|---|---|---|
| Theophylline | 12.0 | 36.8 |
| Kappa carrageenan | 0.2 | 0.6 |
| Locust bean gum | 0.4 | 1.2 |
| Water | 20.0 | 61.3 |

The molded gel tablets were air dried for 24 hours. The dry tablet size was 11.1×4.8 mm and the average tablet weight was 225 mg. The tablet hardness was 8.0 kg and the average tablet density was 0.544.

The dissolution test was carried out at 50 rpm and 37° C. in a 0.1N HCl dissolution medium (pH 1.3). The floating tablets had the following release pattern:

| Time, hours | % Released | Cumulative % |
|---|---|---|
| 1 | 15 | 15 |
| 2 | 17 | 32 |
| 3 | 5 | 37 |
| 4 | 8 | 45 |
| 6 | 13 | 58 |

-continued

| Time, hours | % Released | Cumulative % |
|---|---|---|
| 8 | 7 | 65 |
| 10 | 6 | 71 |
| 12 | 6 | 77 |

EXAMPLE 16

Theophylline tablets were prepared as described in Example 1, using a 2:1 mixture of kappa carrageenan and locust bean gum as the gelling agent, in the following formulation:

| Ingredients | grams | % |
|---|---|---|
| Theophylline | 12.0 | 36.8 |
| Kappa carrageenan | 0.4 | 1.2 |
| Locust bean gum | 0.2 | 0.6 |
| Water | 20.0 | 61.3 |

The molded gel tablets were air dried for 24 hours. The dry tablet size was 10.59×4.27 mm and the average tablet weight was 226 mg. The tablet hardness was 8.0 kg and the average tablet density ws 0.600.

The dissolution test at 50 rpm and 37° C. in a 0.1N HCl dissolution medium showed that the floating tablets had the following release pattern:

| Time, hours | % Released | Cumulative % |
|---|---|---|
| 1 | 24 | 24 |
| 2 | 18 | 42 |
| 3 | 14 | 56 |
| 4 | 13 | 69 |
| 6 | 18 | 87 |
| 8 | 8 | 95 |
| 10 | 5 | 100 |

The foregoing is exemplary and illustrative of compositions and products responding to the present invention, but it is to be understood that they are not limitative since many active medicaments of various types and many different gelling agents can be employed in the new non-compressed tablets.

What is claimed is:

1. A therapeutic composition in unit dosage form as a non-compressed tablet having a network of multitudinous air holes and passages therein and a density of less than one and capable of floating on gastric fluid in vivo and providing sustained release of the therapeutic agent over an extended period of time, comprising a matrix formed from a gelling agent, a therapeutic agent and water, characterized in that, in percentages by weight based on the total weight of the tablet, the latter contains 2 to 6.5% gelling agent, 75 to 92.5% therapeutic agent, 0% oil and the balance is water.

2. The composition according to claim 1 in which the gelling agent is one or more agents selected from the group consisting of agar, agarose and a mixture of locust bean gum with either agar, agarose, alginic acid and carrageenan.

3. A therapeutic composition in unit dosage form as a non-compressed tablet having a network of multitudinous air holes and passages therein and a density of less than one and capable of floating on gastric fluid in vivo and providing sustained release of the therapeutic agent over an extended period of time, comprising a matrix formed from a gelling agent, theophylline and water, characterized in that, in percentages by weight based on the total weight of the tablet, the latter contains 2 to 6.5% gelling agent, 75 to 92.5% theophylline, 0% oil and the balance is water.

4. The composition according to claim 3 in which the gelling agent is one or more agents selected from the group consisting of agar, agarose and a mixture of locust bean gum with either agar, agarose, alginic acid and carrageenan.

5. A method of forming a non-compressed tablet having a network of multitudinous air holes and passages therein and a density of less than one and capable of floating on gastric fluid in vivo and providing sustained release of the therapeutic agent over an extended period of time, which comprises forming a solution of gelling agent in water, cooling said solution but not to the point where gelation takes place, adding a therapeutic agent with stirring, pouring the resultant suspension into a tablet mold and letting it stand in the mold to form a gel, and drying the molded gel tablets to reduce the water content, characterized in that the aqueous solution contains 0.5 to 4% gelling agent, 25 to 40% therapeutic agent, 0% oil and the balance is water, all by weight based on the total weight.

6. A method according to claim 5 in which the gelling agent is one or more agents selected from the group consisting of agar, agarose and a mixture of locust bean gum with either agar, agarose, alginic acid and carrageenan.

7. A method according to claim 5 in which the therapeutic agent is theophylline.

* * * * *